(12) United States Patent
Lee

(10) Patent No.: US 11,110,273 B2
(45) Date of Patent: *Sep. 7, 2021

(54) ELECTRICAL STIMULATION DEVICE

(71) Applicant: Y-BRAIN INC., Daejeon (KR)

(72) Inventor: Kiwon Lee, Seongnam-si (KR)

(73) Assignee: Y-BRAIN INC., Daejeon (KR)

( * ) Notice: Subject to any disclaimer, the term of this patent is extended or adjusted under 35 U.S.C. 154(b) by 188 days.

This patent is subject to a terminal disclaimer.

(21) Appl. No.: 16/428,262

(22) Filed: May 31, 2019

(65) Prior Publication Data

US 2019/0336766 A1    Nov. 7, 2019

Related U.S. Application Data

(63) Continuation-in-part of application No. 15/500,308, filed as application No. PCT/KR2015/006969 on Jul. 6, 2015, now Pat. No. 10,342,969.

(30) Foreign Application Priority Data

Aug. 1, 2014    (KR) ........................ 10-2014-0098777

(51) Int. Cl.
*A61N 1/04* (2006.01)
*A61N 1/36* (2006.01)

(52) U.S. Cl.
CPC ....... *A61N 1/36025* (2013.01); *A61N 1/0456* (2013.01); *A61N 1/0476* (2013.01); *A61N 1/36031* (2017.08)

(58) Field of Classification Search
CPC .............. A61N 1/0484; A61N 1/36014; A61N 1/36025; A61N 1/0529; A61N 1/0526
See application file for complete search history.

(56) References Cited

U.S. PATENT DOCUMENTS

| | | | |
|---|---|---|---|
| 10,342,969 B2 * | 7/2019 | Lee | ................... A61N 1/0484 |
| 2012/0206945 A1 | 8/2012 | Brogan et al. | |
| 2013/0204315 A1 | 8/2013 | Wongsarnpigoon et al. | |

FOREIGN PATENT DOCUMENTS

| KR | 10-2014-0037803 A | 3/2014 |
|---|---|---|
| KR | 10-2014-0080299 A | 6/2014 |

OTHER PUBLICATIONS

International Search Report dated Oct. 13, 2015 corresponding to International Application PCT/KR2015/006969 citing the above reference(s).

* cited by examiner

*Primary Examiner* — Alyssa M Alter
(74) *Attorney, Agent, or Firm* — Hauptman Ham, LLP

(57) ABSTRACT

An electrical stimulation device is provided. The electrical stimulation device according to one embodiment of the present inventive concept is worn on the head so as to apply electrical stimulation to the brain, and comprises: a frame to be worn on the head; an electrode structure including an electrode part formed of a conductive member and a cover unit formed of an insulating member covering at least a part of the electrode part, and of which one end is connected to the frame; and a patch detachable from the electrode structure and making contact with the head when attached to the electrode structure.

10 Claims, 16 Drawing Sheets

ABSTRACT

ELECTRICAL STIMULATION DEVICE

CROSS REFERENCE TO RELATED APPLICATION

The present application is a Continuation in Part of U.S. application Ser. No. 15/500,308, filed on Jan. 30, 2017, which is a National Stage entry of PCT/KR2015/006969, filed on Jul. 6, 2015 and also claims the priorities of Korean Patent Application No. 10-2014-0098777, filed on Aug. 1, 2014 in the KIPO (Korean Intellectual Property Office), the disclosure of which are incorporated herein in their entirety by reference.

TECHNICAL FIELD

The present disclosure relates to a security electrical stimulation device, and more particularly, to an electrical stimulation device worn on a user's head to apply an electrical stimulation to a brain.

BACKGROUND ART

Brain electrical stimulation technologies using transcranial Direct Current Stimulation (tDCS) have been known to be effective on improvement of cognitive ability and mental illness treatments such as depression and Attention Deficit Hyperactivity Disorder (ADHD).

Thus, if the brain electrical stimulation technology can be used in everyday life, brain function may be improved and continuous mental disorders may be treated by activating or inhibiting neuronal connections.

DISCLOSURE

Technical Problem

However, a conventional electrical stimulation apparatus is mainly configured to directly attach a patch to a flexible strap or head cap and then manually adjust the stimulation intensity of the electrical stimulation apparatus. Therefore, the conventional electrical stimulation device is only used intermittently by experts, and ordinary persons who do not have expert knowledge on the configuration and position of the brain and an allowable amount of current could not use the electrical stimulation device in everyday life due to the risk of a safety accident caused by misoperation.

It is an object of the present disclosure to provide an electrical stimulation device which may be safely used in everyday life by ordinary users having no expert knowledge.

It is another object of the present disclosure to provide an electrical stimulation device having superior portability and wearing comfort due to a simple structure.

The technical problems of the present disclosure are not limited to the above-mentioned technical objects, and other technical objects which are not mentioned can be clearly understood by those skilled in the art from the following description.

Technical Solution

In accordance with one aspect of the present disclosure, an electrical stimulation device worn on a head and applying an electrical stimulation to a brain includes a frame worn on the head, an electrode structure comprising an electrode part formed of a conductive member and a cover unit formed of an insulating member covering at least a part of the electrode part, the electrode structure having one end connected to the frame, and a patch detachable from the electrode structure and making contact with the head when attached to the electrode structure.

Advantageous Effects

According to the present disclosure, since a using method is simple, ordinary users having no expert knowledge may safely use the electrical stimulation device in everyday life.

Further, according to the present disclosure, portability and wearing comfort are superior due to a simple structure.

Further, according to the present disclosure, since a user is notified of whether he/she correctly wears an electrical stimulation device, a safety accident due to incorrect wearing may be prevented in advance.

Further, according to the present disclosure, since the position of an electrode structure is controllable and the electrode structure is tiltable, an electrical stimulation may be accurately applied to a target position.

Further, according to the present disclosure, since a patch is detachable to the electrode structure, the patch may be easily replaced.

BEST MODE

Figure 1:
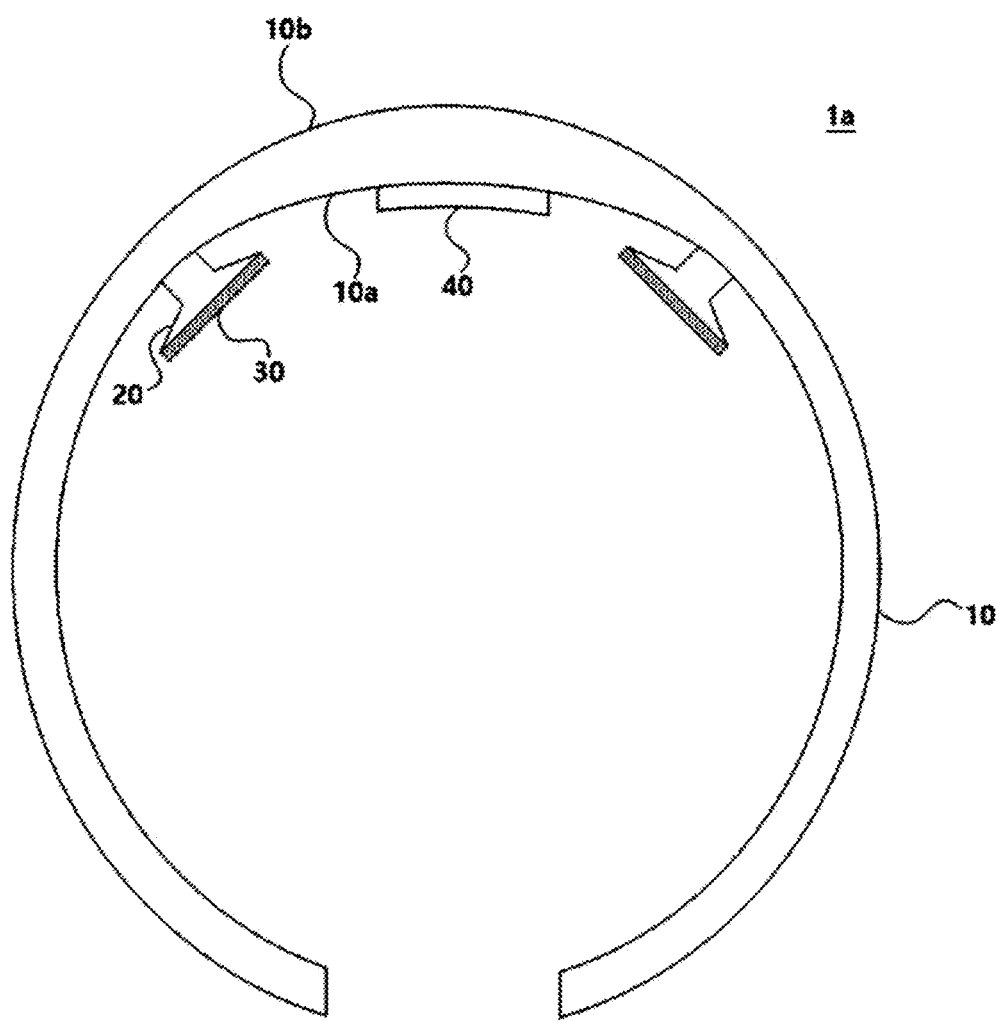
FIG. 1 is a plan view of an electrical stimulation device according to an embodiment of the present disclosure.

The above objects, features and advantages will become apparent from the detailed description with reference to the accompanying drawings. Embodiments are described in sufficient detail to enable those skilled in the art to easily practice the technical idea of the present disclosure. Detailed descriptions of well-known functions or configurations may be omitted in order not to unnecessarily obscure the gist of the present disclosure. Hereinafter, embodiments of the present disclosure will be described in detail with reference to the accompanying drawings. Throughout the drawings, like reference numerals refer to like elements.

Unless defined otherwise, all terms used herein (including technical or scientific terms) have the same meanings as those generally understood by those of ordinary skill in the art to which the present inventive concept may pertain. The terms as those defined in generally used dictionaries are construed to have meanings matching that in the context of related technology and, unless clearly defined otherwise, are not construed to be ideally or excessively formal.

Terms used in the present specification are used for explaining a specific embodiment, not for limiting the present inventive concept. Thus, an expression used in a singular form in the present specification also includes the expression in its plural form unless clearly specified otherwise in context. It will be further understood that the terms "comprises" and/or "comprising" used herein specify the presence of stated features or components, but do not preclude the presence or addition of one or more other features or components.

Hereinafter, an electrical stimulation device according to embodiments of the present disclosure is described with reference to the accompanying drawings.

Figure 2:
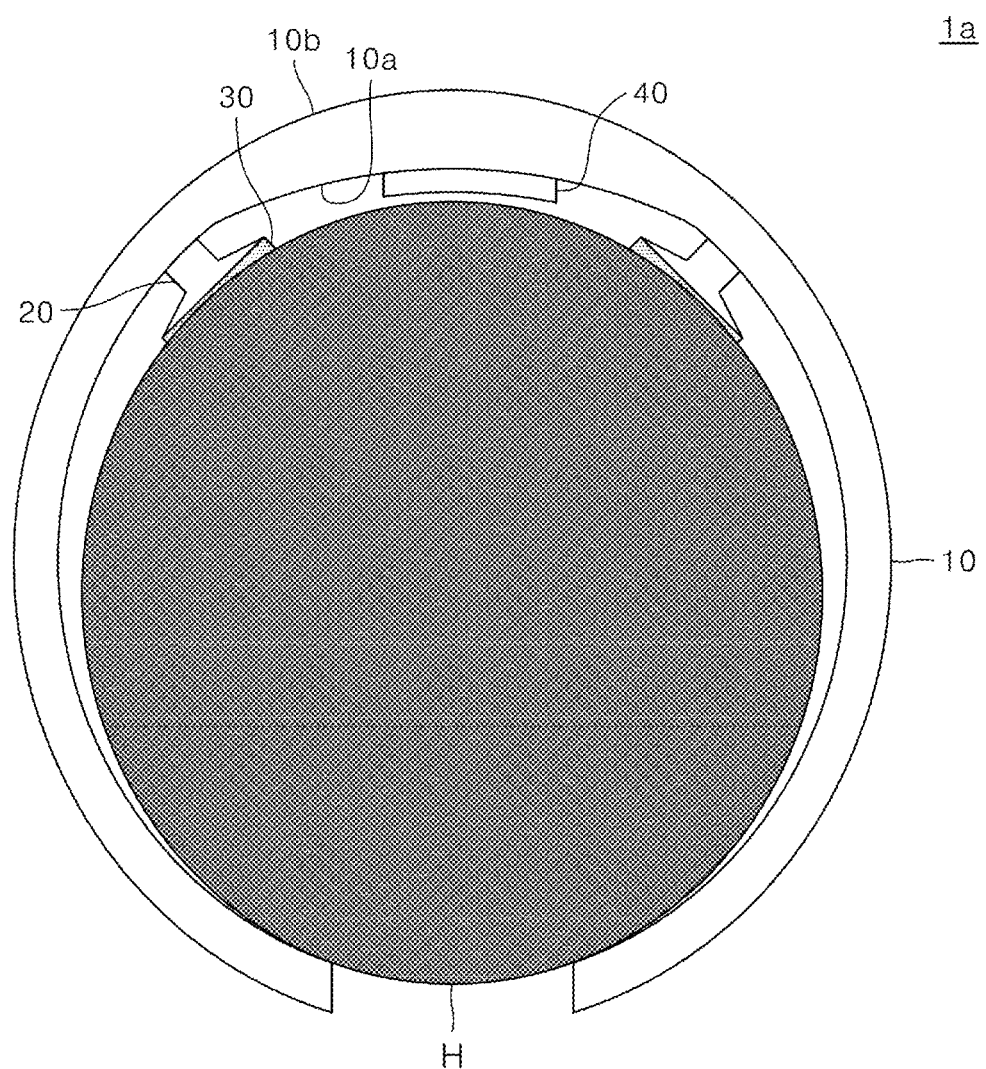
FIG. 2 is a plan view of the electrical stimulation device of FIG. 1 worn on a head.
Figure 3:
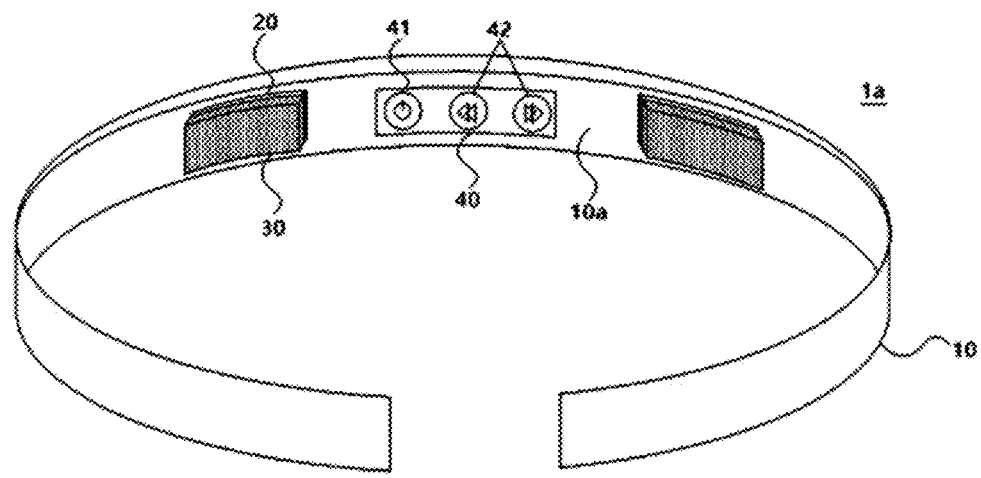
FIG. 3 is a perspective view of the electrical stimulation device of FIG. 1.
Figure 4:
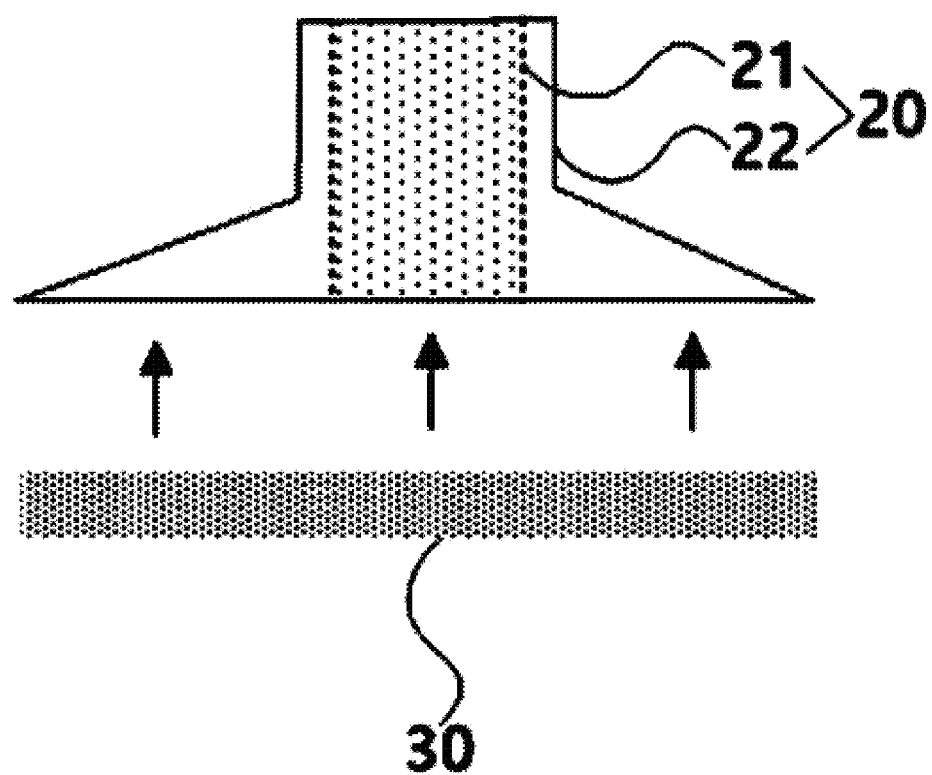
FIG. 4 is a front view of an electrode structure and a patch included in the electrical stimulation device of FIG. 1.
Figure 5:
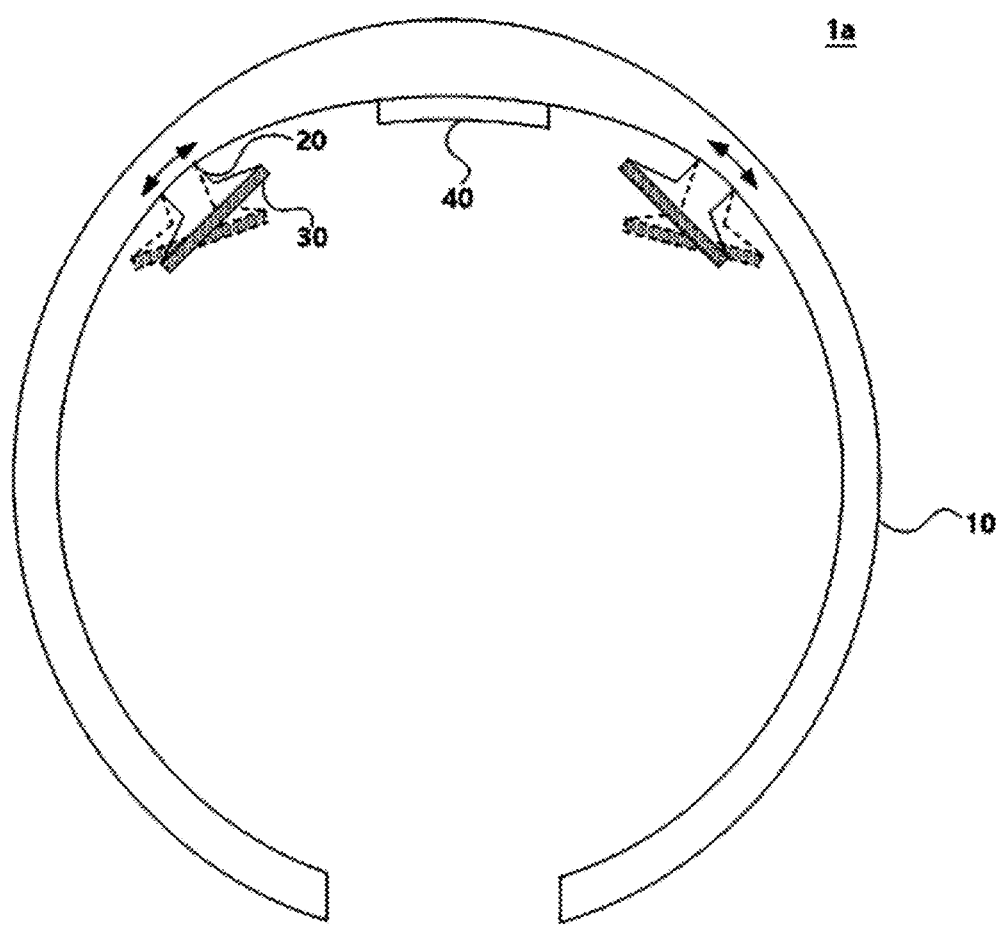
FIG. 5 is a view for explaining tilting of the electrode structure included in the electrical stimulation device of FIG. 1.

First, an electrical stimulation device 1a according to an embodiment of the present disclosure is described with reference to FIGS. 1 to 5. FIG. 1 is a plan view of the electrical stimulation device 1a according to an embodiment of the present disclosure. FIG. 2 is a plan view of the electrical stimulation device 1a of FIG. 1 worn on a head H. FIG. 3 is a perspective view of the electrical stimulation device 1a of FIG. 1. FIG. 4 is a front view of an electrode structure 20 and a patch 30 included in the electrical stimulation device 1a of FIG. 1. FIG. 5 is a view for explaining tilting of the electrode structure 20 included in the electrical stimulation device 1a of FIG. 1.

Referring to FIGS. 1 to 3, the electrical stimulation device 1a according to an embodiment of the present disclosure may be worn on the head H of a user to apply an electrical stimulation to a brain of the user. In detail, when the user simply wears the electrical stimulation device 1a on the head H, the patch 30 may contact a particular position of the head H. Accordingly, current flows to the particular position of the head H of the user through the patch 30 and thus an electrical simulation may be applied to a target area of the brain.

Referring to FIGS. 1 and 4, the electrical stimulation device 1a may include a frame 10, the electrode structure 20, and the patch 30 and, in some embodiments, may further include an operation unit 40. However, since the elements illustrated in FIGS. 1 and 4 are not essential, the electrical stimulation device 1a may include more or less elements compared to the elements illustrated in FIGS. 1 and 4.

The frame 10, as a frame of the electrical stimulation device 1a, may include the electrode structure 20, a power unit (not shown), etc. so that various structures may be coupled to the frame 10 or included in the frame 10. The frame 10 may include a first surface 10a facing the head H and a second surface 10b at the opposite side of the first surface 10a. Furthermore, since the frame 10 is wearable on the head H of a user, the user may use the electrical stimulation device 1a by wearing the same on the head H. Accordingly, the shape of the frame 10 is not limited only if the frame 10 is wearable on the head H of a user.

For example, referring to FIGS. 1 and 3, the frame 10 may have a ring structure with one open side, but the present disclosure is not limited thereto. When the frame 10 is worn on the head H of a user, the frame 10 may press the head H so that the frame 10 may not fall down and may be stably fixed to the head H. In some cases, as a partial area of the frame 10 is supported on an auricle of the user, the frame 10 may be more stably worn on the head H, the present disclosure is not limited thereto.

Since one side of the frame 10 is open, the frame 10 may spread outwardly according to the size of the head H of a user so as to be worn on the head H of a user. Accordingly, according to the electrical stimulation device 1a according to the present embodiment, the user may easily wear the electrical stimulation device 1a without a limitation to the size of the head H of a user.

The electrode structure 20, referring to FIGS. 1 and 4, may include an electrode part 21 formed of a conductive member and a cover unit 22 formed of an insulating member and covering at least a part of the electrode part 21. One end of the electrode structure 20 may be connected to the frame 10 and fixed thereto. In detail, the one end of the electrode structure 20 may be connected to the first surface 10a of the frame 10 and fixed thereto.

The electrode part 21, as an inner area of the electrode structure 20, may be formed of a conductive member. Although the conductive member may be a metal member, the present disclosure is not limited thereto. In detail, the electrode part 21 may receive current from the power unit of the frame 10, and transfer the received current to the patch 30.

The cover unit 22, as an outer area of the electrode structure 20, may be formed of an insulating member. Although the insulating member may include plastic, the present disclosure is not limited thereto. In detail, the cover unit 22 may surround at least a part of the insulating member. Since the cover unit 22 surrounds the electrode part 21, even when current flows in the electrode part 21, the electrical stimulation device 1a may be safely used.

Although the electrical stimulation device 1a of FIG. 1 includes two electrode structures 20, the number of the electrode structures 20 included in the electrical stimulation device 1a is not limited thereto. When an electrical stimulation is needed for one position, one electrode structure may be provided as the electrode structure 20. When an electrical stimulation is needed for a plurality of positions, two or more electrode structures may be provided as the electrode structure 20.

Referring to FIG. 5, since the cover unit 22 of the electrode structure 20 is formed of a flexible member, an area of the electrode structure 20 connected to the frame 10 may be tiltable. In detail, as the electrode structure 20 is tilted according to a user's operation, the direction of the electrode structure 20 may be adjusted. Accordingly, according to the electrical stimulation device 1a of the present embodiment, after wearing the electrical stimulation device 1a, the user may adjust the direction of the electrode structure 20 by tilting the electrode structure 20 such that the patch 30 closely contacts the head H of a user. Accordingly, since the position of the patch 30 may be precisely adjusted, the electrical stimulation device 1a according to an embodiment of the present disclosure may be used conveniently and safely.

The patch 30, referring to FIGS. 1 and 4, may be datable to the electrode structure 20. When attached to the electrode structure 20, the patch 30 may contact the head H. For example, the patch 30 may be attached to the electrode structure 20 by using an adhesive and removed after use, the present disclosure is not limited thereto. The detachment of the electrode structure 20 is described later.

When the user wears the electrical stimulation device 1a, the patch 30 attached to the electrode structure 20 may contact the head H of a user. The patch 30 may receive current from the electrode part 21 and transfer the received current to the head H of a user.

For example, the patch 30 may include chlorine ions. Accordingly, when the patch 30 contacts the head H, impedance of a skin interface is lowered so that the occurrence of pain during an electrical stimulation may be prevented. Since the patch 30 may be in a solid state or a gel state, no electrolyte needs to be separately coated on the scalp during the electrical stimulation, and referring to FIG. 2, the patch 30 may be bent corresponding to the shape of the head H. Accordingly, according to the electrical stimulation device 1a of the present embodiment, use of the electrical stimulation device 1a may be convenient and wearing comfort may be superior.

Referring to FIGS. 1 to 3, the electrical stimulation device 1a may include the operation unit 40 for controlling the operation of an electrical apparatus. For example, the operation unit 40 may include a first operation unit 41 for controlling application of power and a second operation unit 42 for controlling the strength of current flowing in the electrode part 21, the present disclosure is not limited thereto. Accordingly, the user may operate the electrical stimulation device 1a by using the operation unit 40, as necessary.

The frame 10 may include the first surface 10a facing the head H and the second surface 10b at the opposite side of the first surface 10a. The operation unit 40 may be formed on the first surface 10a of the frame 10. In other words, since the operation unit 40 is located on the first surface 10a that is a wearing surface of the frame 10, when the user wears the electrical stimulation device 1a, manipulation of the electrical stimulation device 1a may be prevented during the progress of an electrical stimulation. The manipulation of electrical stimulation device 1a may be possible only when the electrical stimulation device 1a is not worn on the head H. Accordingly, according to the electrical stimulation device 1a of the present embodiment, side effects and safety accidents due to misoperation of the electrical stimulation device 1a may be reduced.

As described above, according to the electrical stimulation device 1a of the present embodiment, since the electrical stimulation device 1a may be used only when the user wears the electrical stimulation device 1a, a using method may be simple so that ordinary users having no expert knowledge may safely use the electrical stimulation device 1a in everyday life. Further, according to the present disclosure, portability and wearing comfort are superior due to a simple structure.

Figure 6:
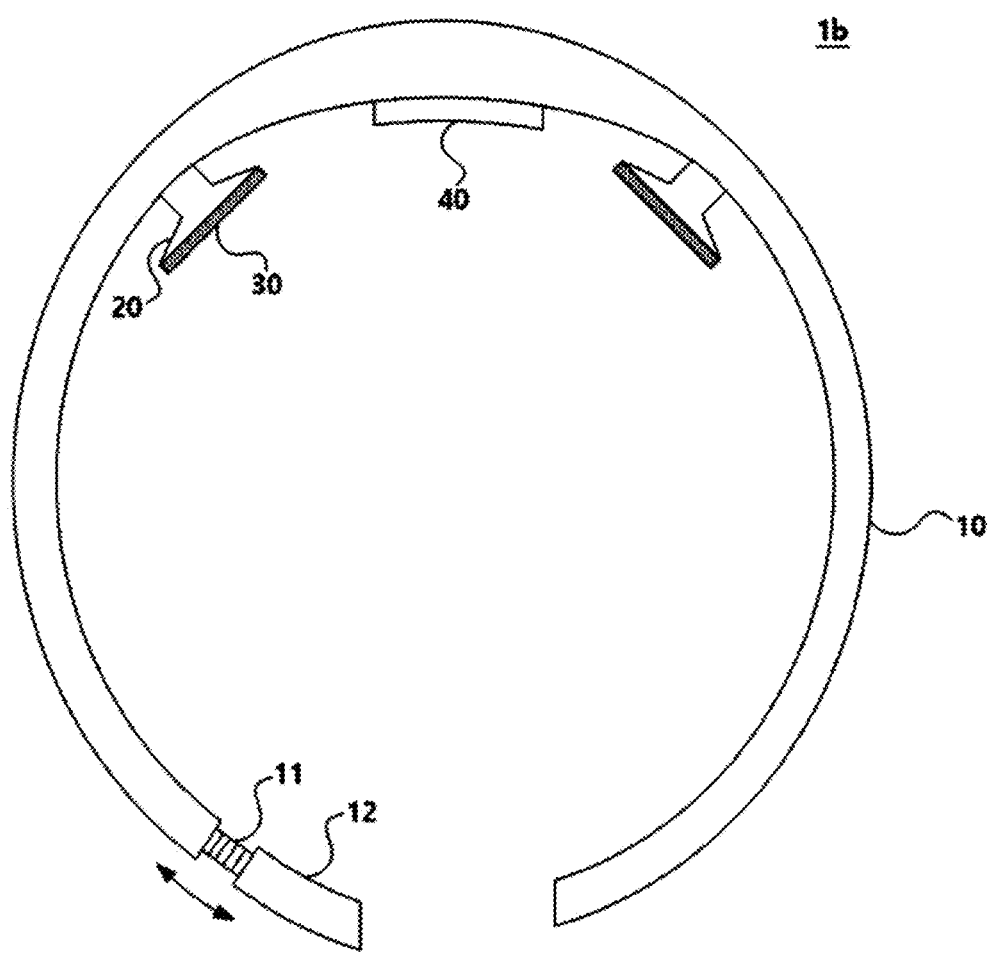
FIG. 6 is a plan view of an electrical stimulation device according to another embodiment of the present disclosure.

An electrical stimulation device 1b according to another embodiment of the present disclosure is described below with reference to FIG. 6. FIG. 6 is a plan view of the electrical stimulation device 1b according to another embodiment of the present disclosure. However, the following description mainly focuses on differences from the electrical stimulation device 1a according to the above-described embodiment.

Referring to FIG. 6, the frame 10 may have a ring shape with one open side and may extend by a preset length along the circumference of the frame 10. In detail, the frame 10 may include an extension shaft 11 and an extension frame 12, and the extension frame 12 may be separated from the frame 10. Accordingly, when the size of the frame 10 is to be adjusted, the user may separate the extension frame 12 coupled to the frame 10 away from the frame 10 along the extension shaft 11. Accordingly, the overall size of the electrical stimulation device 1b may be extended by the length of the extension shaft 11 that is a preset length.

As described above, the electrical stimulation device 1b according to another embodiment of the present disclosure, since the electrical stimulation device 1b is a variable type capable of adjusting the size thereof, the electrical stimulation device 1b may be used by various users.

Figure 7:
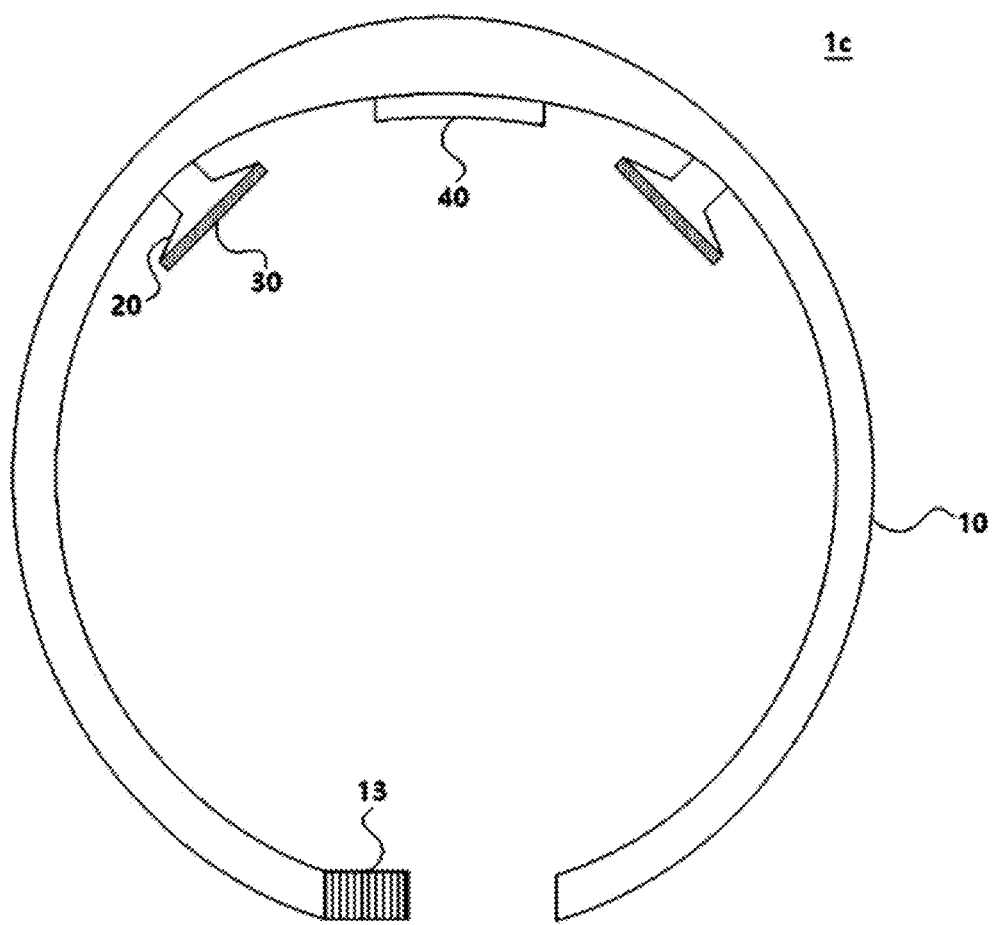
FIG. 7 is a plan view of an electrical stimulation device according to another embodiment of the present disclosure.

Referring to FIG. 7, an electrical stimulation device 1c according to another embodiment of the present disclosure is described. FIG. 7 is a plan view of the electrical stimulation device 1c according to another embodiment of the present disclosure. However, the following description mainly focuses on differences from the electrical stimulation device 1b according to the above-described embodiment.

In FIG. 6, the overall size of the electrical stimulation device 1b according to another embodiment of the present disclosure is adjusted by moving the extension shaft 11 along the extension frame 12. In contrast, in FIG. 7, the overall size of the electrical stimulation device 1c according to the present embodiment may be adjusted by separately connecting a sub-frame 13 to the frame 10.

In detail, referring to FIG. 7, the frame 10 may have a ring shape with one open side, and may be extendable along the circumference of the frame 10 by a preset length. When the size of the frame 10 is to be adjusted, the user may connect separately the sub-frame 13 to one end of the frame 10. There is no limit in the method of connecting the sub-frame 13 to the frame 10. Accordingly, the overall size of the electrical stimulation device 1c may be extendable by the length of the sub-frame 13 that is a preset length.

As described above, according to the electrical stimulation device 1c of the present embodiment, since the electrical stimulation device 1c is a variable type capable of adjusting the size thereof, the electrical stimulation device 1c may be used by various users.

Figure 8:
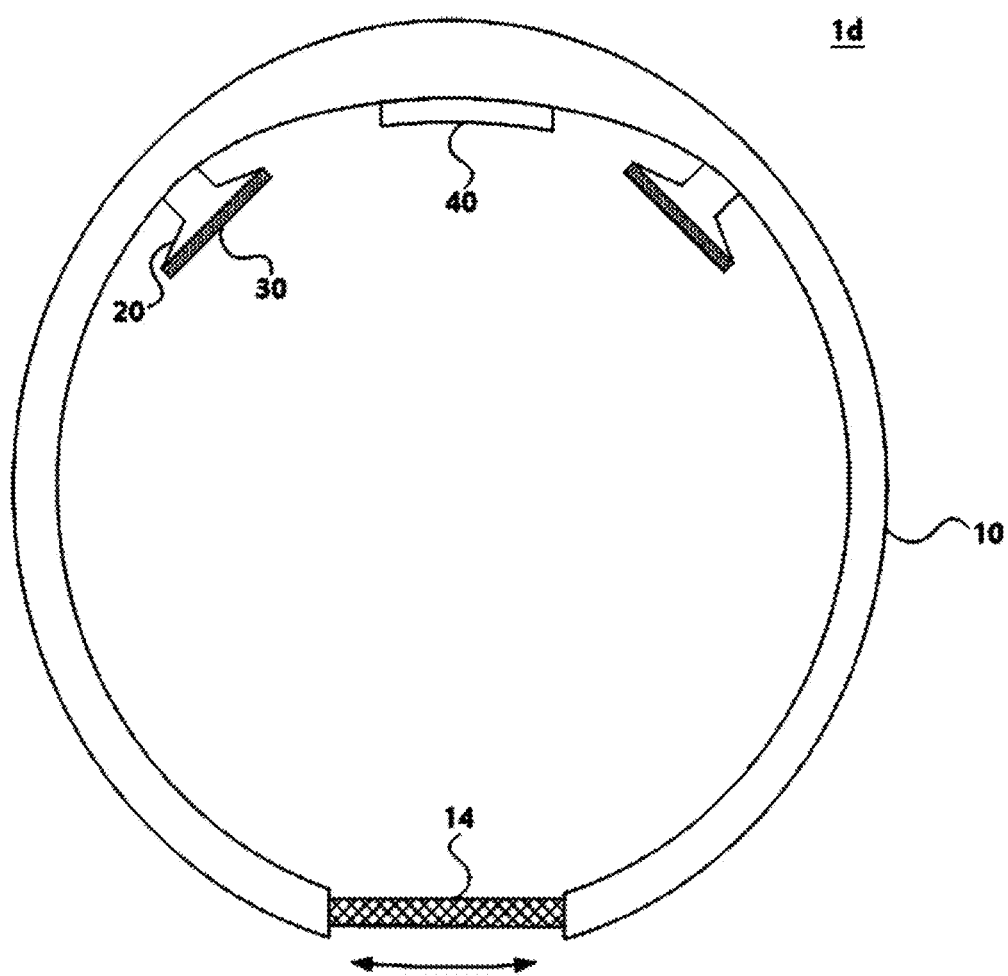
FIG. 8 is a plan view of an electrical stimulation device according to another embodiment of the present disclosure.

Referring to FIG. 8, an electrical stimulation device 1d according to another embodiment of the present disclosure is described. FIG. 8 is a plan view of the electrical stimulation device 1d according to another embodiment of the present disclosure. However, the following description mainly focuses on differences from the electrical stimulation device 1a according to the above-described embodiment.

Referring to FIG. 8, the frame 10 may have a ring shape, and the length of at least a part of the frame 10 may extend along the circumference of the frame 10. In detail, the frame 10 may include an extension part 14. The extension part 14 may be formed of an elastic material unlike the material of the frame 10, so that the length of the extension part 14 may be extendable, but the present disclosure is not limited thereto. Accordingly, when the user wears the frame 10, the length of the extension part 14 may extend along the circumference of the frame 10 to fit to the size of the head H of a user.

Accordingly, according to the electrical stimulation device 1d of the present embodiment, since the size of the frame 10 is adjusted by the extension part 14 to fit to the size of the head H of a user, the user may easily and stably wear the electrical stimulation device 1d. Since the electrical stimulation device 1d is a variable type capable of adjusting the size thereof, the electrical stimulation device 1d may be used by various users.

Figure 9:
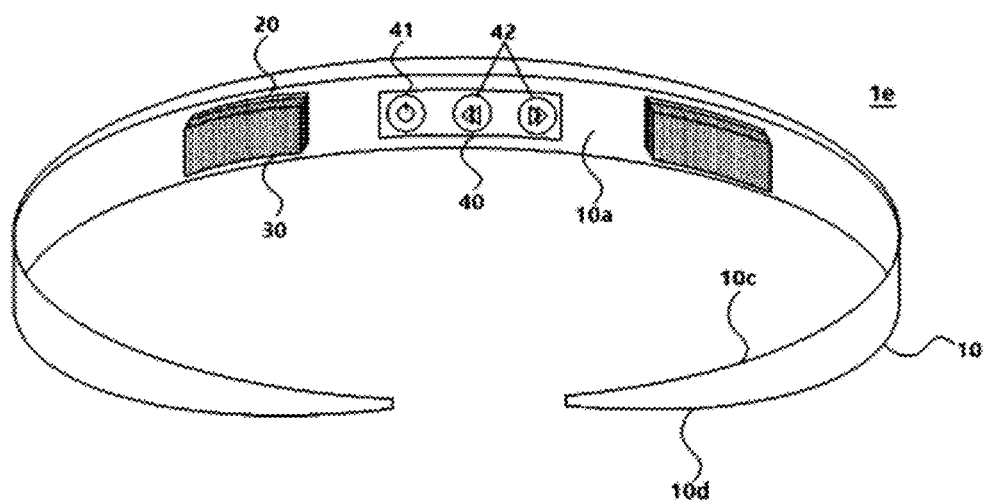
FIG. 9 is a perspective view of an electrical stimulation device according to another embodiment of the present disclosure.

Referring to FIG. 9, an electrical stimulation device 1e according to another embodiment of the present disclosure is described. FIG. 9 is a perspective view of the electrical stimulation device 1e according to another embodiment of the present disclosure. However, the following description mainly focuses on differences from the electrical stimulation device 1a according to the above-described embodiment.

Referring to FIG. 9, the frame 10 may have a vertically asymmetrical shape in a state of being worn on the head H. For example, the thickness of the frame 10 may not be constant and may decrease toward the open side. In detail, the frame 10 may include an upper surface 10c and a lower surface 10d, one of which may be inclined. For example, while the upper surface 10c of the frame 10 may not be inclined, the lower surface 10d of the frame 10. Accordingly, the user may distinguish the upper and lower sides of the electrical stimulation device 1e by visually checking the inclination of the lower surface 10d of the frame 10. Furthermore, the user may distinguish the upper and lower sides of the electrical stimulation device 1e by checking the inclination of the lower surface 10d of the frame 10 with a sense of touch in a state of wearing the electrical stimulation device 1e on the head H.

Accordingly, according to the electrical stimulation device 1e of the present embodiment, since the user may distinguish the upper and lower sides of the electrical stimulation device 1e visually or with a sense of touch, a safety accident due to incorrect wearing of the electrical stimulation device 1e may be prevented in advance.

Figure 10:
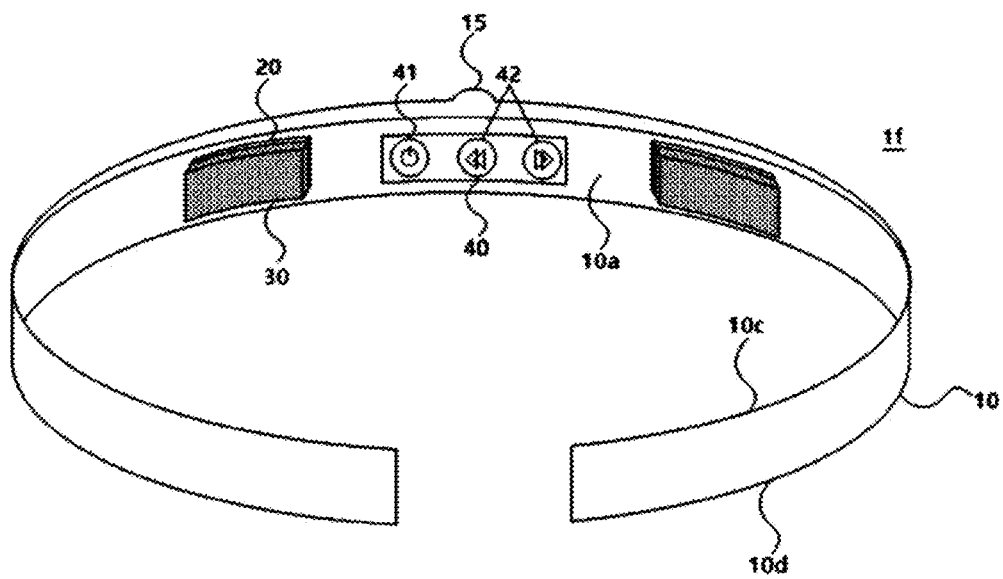
FIG. 10 is a perspective view of an electrical stimulation device according to another embodiment of the present disclosure.

An electrical stimulation device if according to another embodiment of the present disclosure is described with reference to FIG. 10. FIG. 10 is a perspective view of the electrical stimulation device if according to another embodiment of the present disclosure. However, the following description mainly focuses on differences from the electrical stimulation device 1e according to the above-described embodiment.

In FIG. 9, as any one of the upper surface 10c and the lower surface 10d of the frame 10 is inclined, the frame 10 has a vertically asymmetrical shape. In contrast, referring to FIG. 10, the frame 10 may have a vertically asymmetrical shape in a state of being worn on the head H, and a marker 15 may be formed on the upper surface 10c of the frame 10. Accordingly, as the user checks the marker 15 visually or with a sense of touch, the user may distinguish the upper and lower sides of the electrical stimulation device if. Although FIG. 10 illustrates that the marker 15 has a protruding shape, the shape of the marker 15 is not limited only if the marker 15 has a shape that may be distinguished visually or with a sense of touch.

Accordingly, according to the electrical stimulation device if of the present embodiment, since the user may distinguish the upper and lower sides of the electrical stimulation device if visually or with a sense of touch, a safety accident due to incorrect wearing of the electrical stimulation device if may be prevented in advance.

Figure 11:
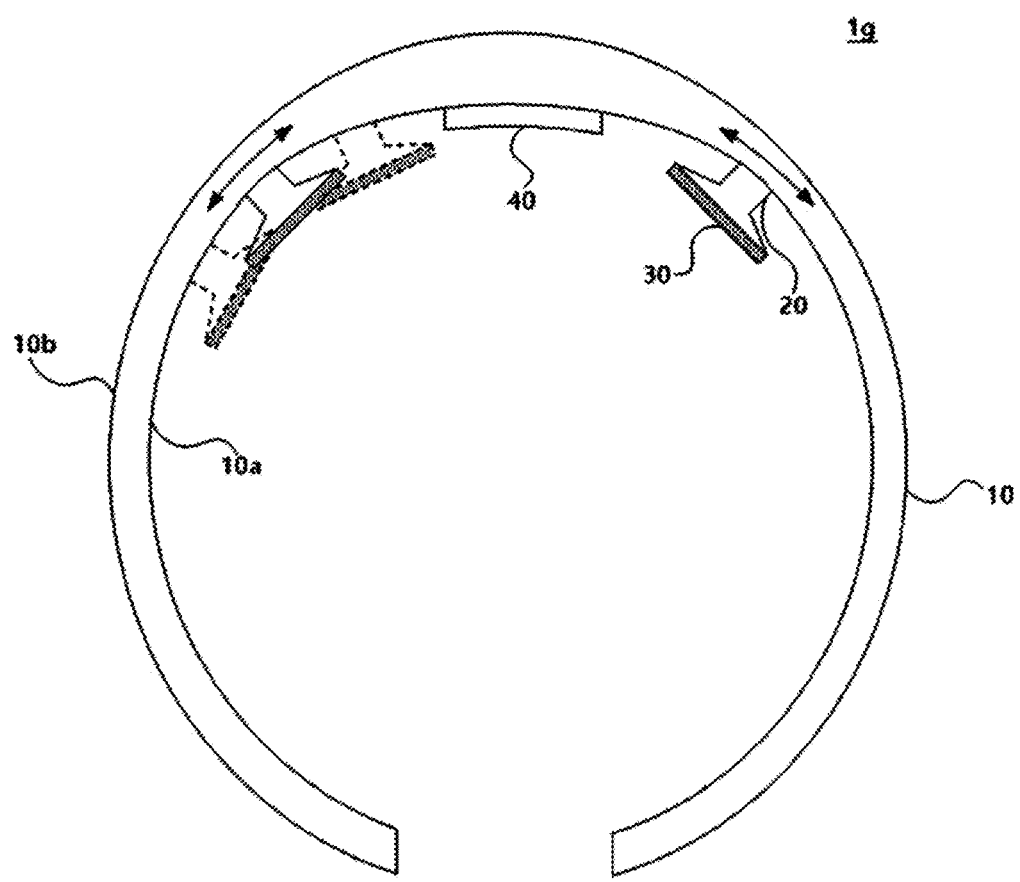
FIG. 11 is a plan view of an electrical stimulation device according to another embodiment of the present disclosure.

An electrical stimulation device 1g according to another embodiment of the present disclosure is described with reference to FIG. 11. FIG. 11 is a plan view of the electrical stimulation device 1g according to another embodiment of the present disclosure. However, the following description mainly focuses on differences from the electrical stimulation device 1a according to the above-described embodiment.

Referring to FIG. 11, the position where the one end of the electrode structure 20 is connected to the frame 10 may be adjusted. In other words, a fixed position of the electrode structure 20 on the frame 10 may be changed.

For example, the frame 10 may include the first surface 10a facing the head H of a user and the second surface 10b at the opposite side of the first surface 10a, The one end of the electrode structure 20 may be connected to the first surface 10a of the frame 10. In this state, while being connected to the first surface 10a, the one end of the electrode structure 20 slides on the first surface 10a so that the position of the one end of the electrode structure 20 connected to the frame 10 may be adjusted. Although FIG. 11 illustrates that the position of the electrode structure 20 is adjustable within a certain area, the present disclosure is not limited thereto and the electrode structure 20 may be moved across the entire area of the frame 10 along the circumference of the frame 10.

According to the electrical stimulation device 1g of the present embodiment, since the position of the electrode structure 20 is adjustable, the position of the patch 30 attached to the electrode structure 20 may be adjusted accordingly. Accordingly, since the electrode structure 20 may be moved to a position where an electrical stimulation is needed according to the purpose of each user, the position of an electrical stimulation may be accurately set according to the user.

Figure 12:
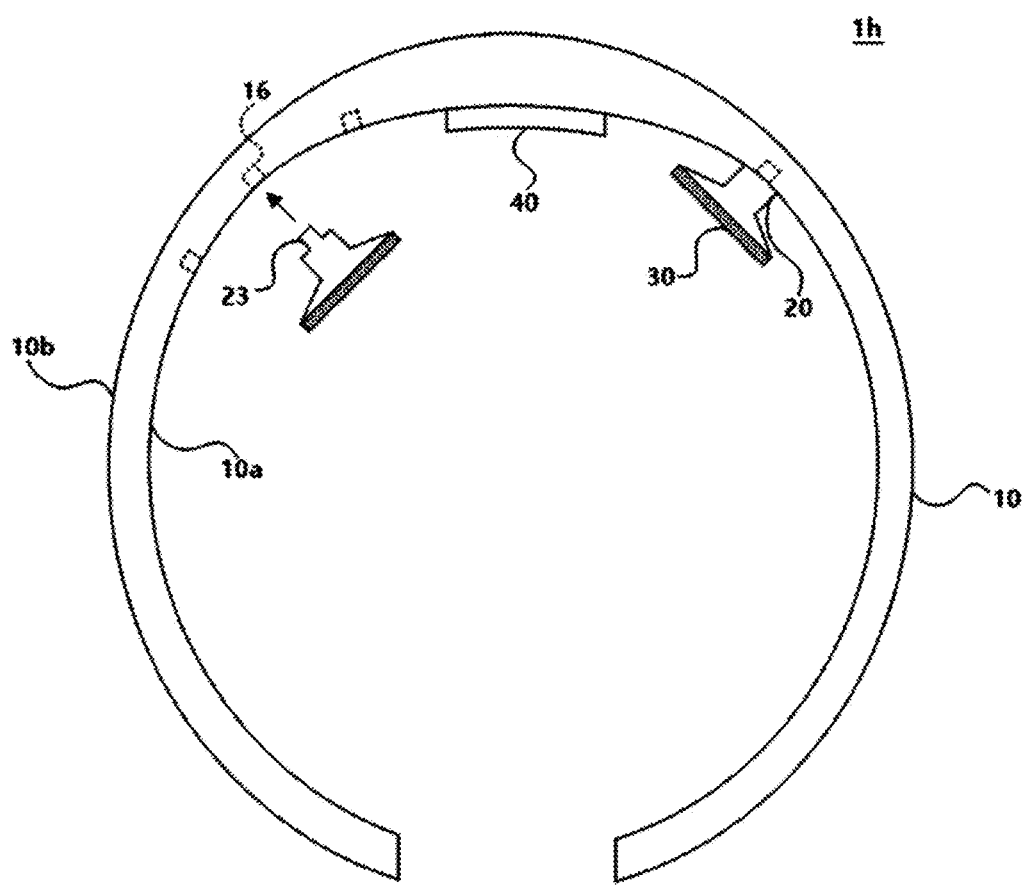
FIG. 12 is a plan view of an electrical stimulation device according to another embodiment of the present disclosure.

An electrical stimulation device 1h according to another embodiment of the present disclosure is described with reference to FIG. 12. FIG. 12 is a plan view of the electrical stimulation device 1h according to another embodiment of the present disclosure. However, the following description mainly focuses on differences from the electrical stimulation device 1a according to the above-described embodiment.

Referring to FIG. 12, the position where the one end of the electrode structure 20 is connected to the frame 10 is previously set to be two or more. The position where the one end of the electrode structure 20 is connected to the frame 10 may be adjustable among the previously set positions.

For example, the frame 10 may include a plurality of first coupling parts 16, and the first coupling parts 16 may be arranged at preset positions on the first surface 10a of the frame 10. If necessary, the first coupling parts 16 may be arranged across the entire area of the frame 10, but the present disclosure is not limited thereto.

The electrode structure 20 may include a second coupling part 23. In detail, the second coupling part 23 may be formed on the one end of the electrode structure 20, the present disclosure is not limited thereto. Although FIG. 12 illustrates that the first coupling parts 16 of the frame 10 has a concave shape and the second coupling part 23 of the electrode structure 20 has a convex shape, the shapes or materials of the first coupling parts 16 of the frame 10 and the second coupling part 23 of the electrode structure 20 are not limited only if they can be complementarily coupled to each other.

According to the electrical stimulation device 1h of the present embodiment, since the position of the electrode structure 20 is adjustable, the position of the patch 30 attached to the electrode structure 20 may be adjusted accordingly. Accordingly, since the electrode structure 20 may be moved to a position where an electrical stimulation is needed according to the purpose of each user, the position of an electrical stimulation may be accurately set according to the user.

Figure 13:
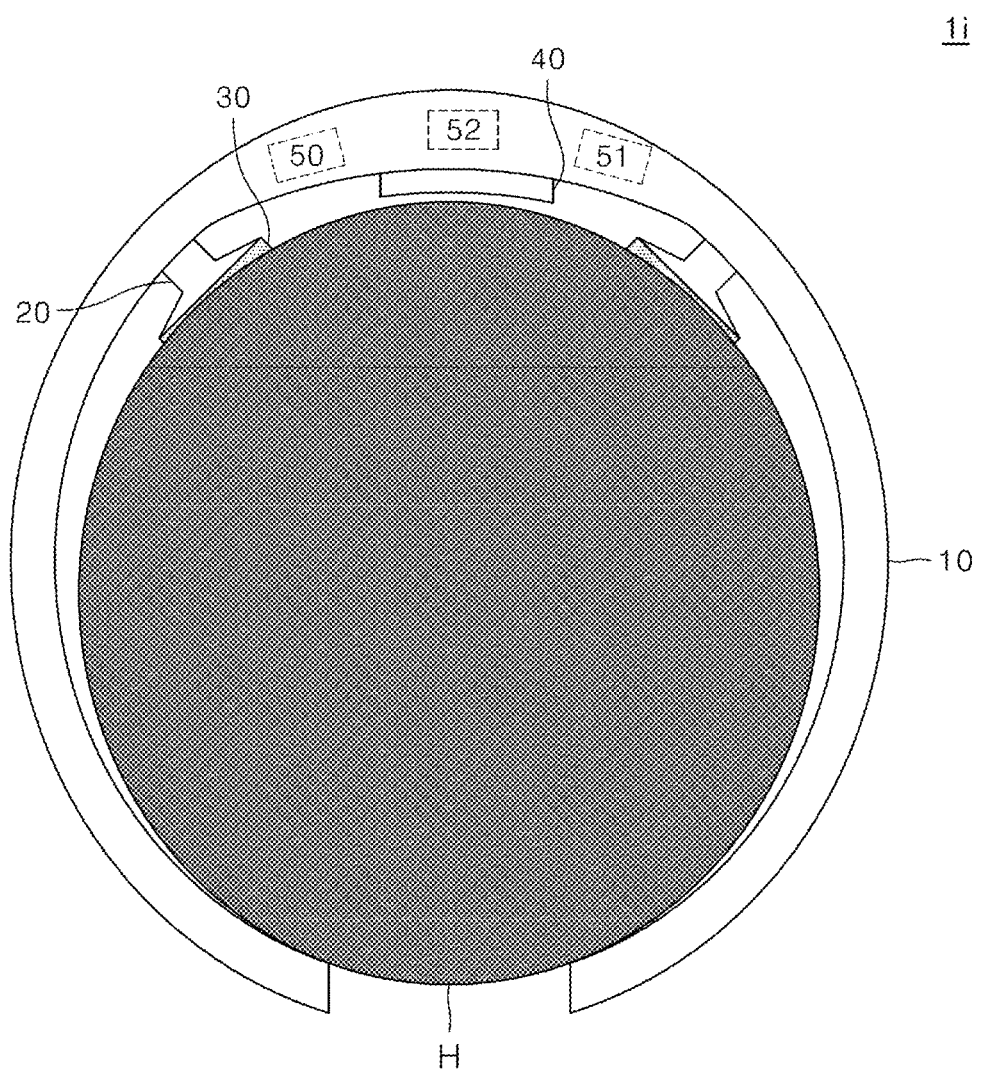
FIG. 13 is a plan view of an electrical stimulation device according to another embodiment of the present disclosure.

An electrical stimulation device 1i according to another embodiment of the present disclosure is described with reference to FIG. 13. FIG. 13 is a plan view of the electrical stimulation device 1i according to another embodiment of the present disclosure. However, the following description mainly focuses on differences from the electrical stimulation device 1a according to the above-described embodiment.

Referring to FIG. 13, the electrical stimulation device 1*i* may further include a wear sensing part 50 for sensing a wear state of the frame 10, an impedance measurement part 51 for measuring impedance through the patch 30, and a controller 52 for determining whether to apply current to the electrode part 21 based on a result of the sensing of the wear sensing part 50 and a result of the measurement of the impedance measurement part 51.

In detail, the wear sensing part 50 senses a worn state of the frame 10 so that the user may identify whether the frame 10 is worn in a correct direction according to the using method. In detail, the wear sensing part 50 may sense whether the user incorrectly wears the frame 10, for example, the electrical stimulation device 1*i* is worn upside down. To this end, the wear sensing part 50 may include a gyro sensor capable of sensing a direction, but the present disclosure is not limited thereto. For example, whether the user wears the electrical stimulation device 1*i* in a correct direction may be determined from the direction sensed by the gyro sensor included in the wear sensing part 50.

The impedance measurement part 51 may measure impedance through the patch 30. In detail, when the user wears the electrical stimulation device 1*i*, the patch 30 contacts the head H and thus the impedance measurement part 51 may measure bioimpedance or electrode impedance through the patch 30. Since there is an impedance value expected when the user correctly wears the electrical stimulation device 1*i*, whether the user correctly wears the electrical stimulation device 1*i* so that the patch 30 closely contacts a target position may be determined through a result of the measurement of the impedance measurement part 51.

The controller 52 may determine whether to apply current to the electrode part 21, based on the result of the sensing of the wear sensing part 50 and the result of the measurement of the impedance measurement part 51. In other words, after receiving the result of the sensing of the wear sensing part 50 and the result of the measurement of the impedance measurement part 51, the controller 52 may analyze the results of the sensing and measurement and, when it is determined that the user wears the electrical stimulation device 1*i* in a correct direction and a measured impedance value is within a preset value range so that the patch 30 is accurately located at the target position, the controller 52 may apply current to the electrode part 21. However, when the user's wear state is determined to be incorrect as a result of the analysis, the controller 52 may not apply current to the electrode part 21.

According to the electrical stimulation device 1*i* of the present embodiment, since the controller 52 automatically starts stimulation by sensing the user's wear state, the user may safely use the electrical stimulation device 1*i*.

Figure 14:
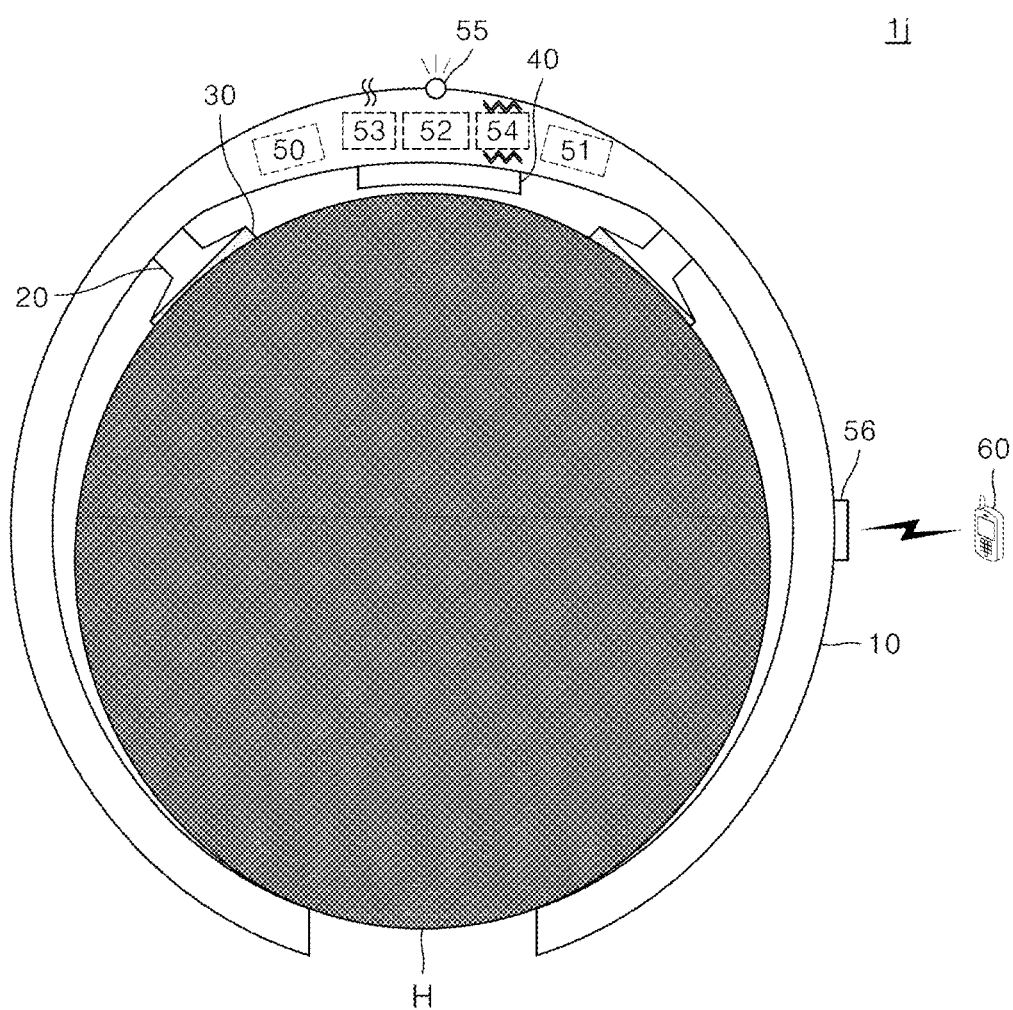
FIG. 14 is a plan view of an electrical stimulation device according to another embodiment of the present disclosure.

An electrical stimulation device 1*j* according to another embodiment of the present disclosure is described with reference to FIG. 14. FIG. 14 is a plan view of the electrical stimulation device 1*j* according to another embodiment of the present disclosure. However, the following description mainly focuses on differences from the electrical stimulation device 1*i* according to the above-described embodiment.

Referring to FIG. 14, the electrical stimulation device 1*j* may further include one or more of a speaker 53, a vibrator 54, a light-emitting device 55, and a communication part 56. The controller 52 may control one or more of the speaker 53, the vibrator 54, the light-emitting device 55, and the communication part 56, based on the result of the sensing of the wear sensing part 50 and the result of the measurement of the impedance measurement part 51.

First, when the controller 52 determines based on based on the result of the sensing of the wear sensing part 50 and the result of the measurement of the impedance measurement part 51 that the user's wear state is incorrect because the user wears the electrical stimulation device 1*j* in the opposite direction or the measured impedance value is not within the preset value range, the controller 52 may give a feedback to the user by controlling one or more of the speaker 53, the vibrator 54, the light-emitting device 55 and the communication part 56.

For example, the controller 52 may guide the user to correctly wear the electrical stimulation device 1*j* by controlling the speaker 53 to generate a warning sound or a guide message. Furthermore, the controller 52 may control the vibrator 54 to generate vibration to thus notify the user of an incorrect wear state. The type of vibration according to the incorrect wear notification may be preset. The controller 52 may control the light-emitting device 55 to generate light to thus the user of an incorrect wear state. The type of light emission according to the incorrect wear notification may be preset. In addition, the controller 52 may control the communication part 56 to notify the user of an incorrect wear state through an external communication terminal 60. The user may check the incorrect wear state of the electrical stimulation device 1*j* by checking the external communication terminal 60.

Accordingly, according to the electrical stimulation device 1*j* of the present embodiment, since the user directly checks that the wear state of the electrical stimulation device 1*j* is incorrect, the risk of a safety accident caused by the incorrect wear of the electrical stimulation device 1*j* may be reduced.

The controller 52 stops the electrical stimulation when the electrical stimulation device 1*j* is not correctly worn even after a preset time period passes after checking the incorrect wear of the electrical stimulation device 1*j*, thereby preventing a safety accident in advance.

The controller 52 an operating state of the electrical stimulation device 1*j* such as start, progress, and end of the electrical stimulation, by controlling any one of the speaker 53, the vibrator 54, and the light-emitting device 55. For example, the controller 52 may guide the start, progress, and end of the electrical stimulation by generating sound through the speaker 53, generating vibration through the vibrator 54, or emitting light through the light-emitting device 55. To this end, the type of sound, vibration, and light emission indicating the start, progress, and end of the electrical stimulation may be previously set.

In addition, the controller 52 may provide the operating state of the electrical stimulation device 1*j* such as the start, progress, and end of the electrical stimulation to the external communication terminal 60 through the communication part 56. In other words, the communication part 56 may transmit the start, progress, and end of the electrical stimulation to the external communication terminal 60.

Accordingly, according to the electrical stimulation device 1*j* of the present embodiment, since the user and other people nearby may directly check the operating state of the electrical stimulation device 1*j*, the electrical stimulation device 1*j* may be conveniently used.

The controller 52 may sense the position of the electrode structure 20 on the frame 10 and transmit the information to the external communication terminal 60 through the communication part 56. Accordingly, the user may check whether the patch 30 is arranged at an accurate position through a display of the external communication terminal 60.

Figure 15:
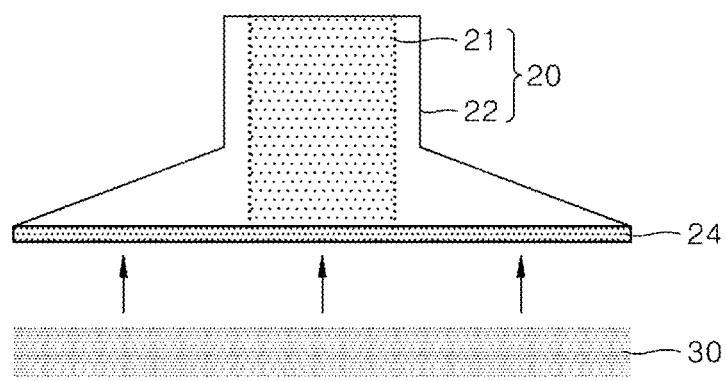
FIG. 15 is a view for explaining an example of a coupling of a patch and the electrode structure included in the electrical stimulation device of FIG. 1.

The coupling of the patch 30 and the electrode structure 20 included in the electrical stimulation device 1*a* of FIG. 1 is described with reference to FIG. 15. FIG. 15 is a view for explaining an example of the coupling of the patch 30 and the electrode structure 20 included in the electrical stimulation device 1*a* of FIG. 1.

Referring to FIG. 15, the patch 30 may be attached to the electrode structure 20 via a coupling part formed of a conductive material. In detail, the electrode structure 20 may include a magnet part 24 as the coupling part. Since the patch 30 may be attached to the magnet part 24 of the electrode structure 20, the patch 30 may be detachable the electrode structure 20. Accordingly, since the patch 30 is replaceable and the magnet part 24 is a conductive member, when the magnet part 24 connects the electrode part 21 of the electrode structure 20 and the patch 30, the current of the electrode part 21 is transferred to the patch 30, the operation of the electrical stimulation device 1*a* is not prohibited.

However, in some embodiments, the magnet part 24 may be formed on the patch 30, not on the electrode structure 20, and may be formed on both of the electrode structure 20 and the patch 30, when necessary.

Figure 16:
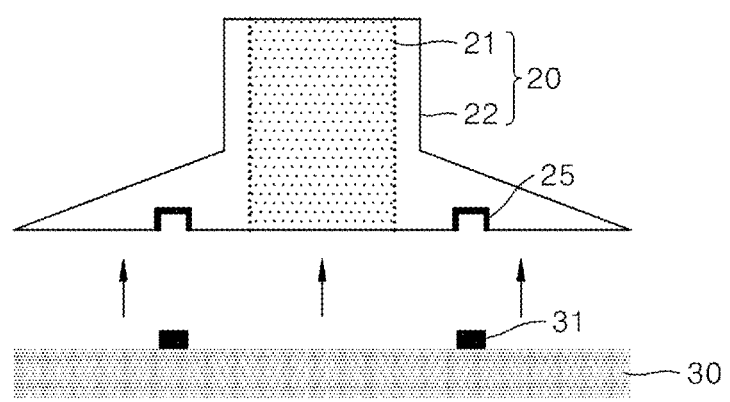
FIG. 16 is a view for explaining another example of a coupling of a patch and the electrode structure included in the electrical stimulation device of FIG. 1.

The coupling of the patch 30 and the electrode structure 20 included in the electrical stimulation device 1*a* of FIG. 1 is described with reference to FIG. 16. FIG. 16 is a view for explaining another example of the coupling of the patch 30 and the electrode structure 20 included in the electrical stimulation device 1*a* of FIG. 1. However, the following description mainly focuses on differences from the coupling of the electrode structure 20 and the patch 30 of FIG. 15.

Referring to FIG. 16, the electrode structure 20 may include a first coupling part 25, and the patch 30 may include a second coupling part 31. The patch 30 may be attached to the electrode structure 20 via the first and second coupling parts 25 and 31 formed of a conductive material. The first and second coupling parts 25 and 31 may be coupled to each other in a complementary structure and may be freely separated from each other as necessary. Accordingly, since the patch 30 may be replaceable and the first and second coupling parts 25 and 31 are conductive members, the operation of the electrical stimulation device 1*a* is not prohibited.

However, the material of the first and second coupling parts 25 and 31 is not limited to a conductive material The markers indicate the proper direction of wearing the electrical stimulation device when the user looks at the electrical stimulation device before wearing the electrical stimulation device, or the direction/position/contact status for warnings about improper wearing with an electrical stimulation device. After wearing the electrical stimulation device, the marker checks the direction, position, and contact state with the mobile phone or outputs the measured result to the mobile phone.

Alternatively, the display portion of the surface of the electrical stimulation device can display the suitability for wearing. As an exemplary embodiment, the electrical stimulation device can check the wearing state using built-in sensor. Alternatively, an external cell phone camera can be used to track the marker on the electrical stimulation device to measure the wear status.

When the display mode is selected, the display portion of the electrical stimulation device surface may immediately change the output information so that the user can recognize the improper wearing state of the electrical stimulation device. Also, the user can check the wearing state of the electrical stimulation device through the guidance through the mobile phone.

Marker, on the other hand, can be placed with physical shape on the electrical stimulation device. In this case, judging whether wearing is proper can be judged by using the built-in sensor in the electrical stimulation device. Also, it is possible to recognize the wearing condition of marker by using an external mobile phone camera. If the electrical stimulation device is improperly worn, it can provide information via the mobile phone instead of immediate changes in the device's appearance.

In another embodiment, a virtual marking scheme existing within a cellular phone camera image may be used. In this case, there is no or minimal physical marker on the surface of the actual electrical stimulation device. Also, the wearing state of the electrical stimulation device can be recognized using an external cellular phone camera. In this case, information can be provided as if the marker has actually been changed by overlaying the necessary information on the camera image. It has the advantages of less restrictions on product design and the ability to dynamically provide more information based on a mobile phone.

The present disclosure described above may be variously substituted, altered, and modified by those skilled in the art to which the present inventive concept pertains without departing from the scope and sprit of the present disclosure. Therefore, the present disclosure is not limited to the above-mentioned exemplary embodiments and the accompanying drawings.

What is claimed:

1. An electrical stimulation device configured to be worn on a human head, the electrical stimulation device comprising:
   a frame having an inner surface and an outer surface opposite to the inner surface, and configured to be worn on the human head;
   an a plurality of electrode structures installed on the inner surface of the frame, and configured to apply an electrical stimulation to a brain of the human head, wherein each electrode structure of the plurality of electrode structures comprises an electrode part formed of a conductive member and a cover unit formed of an insulating member surrounding at least a part of the electrode part, and one end of the electrode structure is connected to the inner surface of the frame;
   a plurality of patches coupled with the plurality of the electrode structures, wherein each patch of the plurality of patches is attached to the other end of corresponding electrode structure so as to be detachable from the corresponding electrode structure; and
   an operation unit installed on the inner surface of the frame, and configured to control an operation of the electrical stimulation device, wherein a marker is formed on the upper or lower surface of the frame.

2. The electrical stimulation device of claim 1, the marker is a protruding shape.

3. The electrical stimulation device of claim 1, wherein the frame has a ring shape with one open side and a length of at least a part of the frame extends along a circumference of the frame.

4. The electrical stimulation device of claim 3, wherein the frame comprises an extension shaft and an extension frame, wherein the extension frame is separated from the frame.

5. The electrical stimulation device of claim 3, wherein the frame is connected to an sub-frameshaft at one end of the frame.

6. The electrical stimulation device of claim 3, wherein the frame is connected to an sub-frameshaft at one end of the frame.

7. The electrical stimulation device of claim 1, wherein the frame has a ring shape and a length of at least a part of the frame extends along a circumference of the frame, and the frame comprises extension part, and wherein the extension part is formed of an elastic material which is differ from the material of the frame.

8. An electrical stimulation device configured to be worn on a human head, the electrical stimulation device comprising:
- a frame having an inner surface and an outer surface opposite to the inner surface, and configured to be worn on the human head; an a plurality of electrode structures installed on the inner surface of the frame, and configured to apply an electrical stimulation to a brain of the human head, wherein each electrode structure of the plurality of electrode structures comprises an electrode part formed of a conductive member and a cover unit formed of an insulating member surrounding at least a part of the electrode part, and one end of the electrode structure is connected to the inner surface of the frame;
- a plurality of patches coupled with the plurality of electrode structures, wherein each patch of the plurality of patches is attached to the other end of corresponding electrode structure so as to be detachable from the corresponding electrode structure;
- an operation unit installed on the inner surface of the frame, and configured to control an operation of the electrical stimulation device; a wear sensing part configured to sense a worn state of the frame;
- an impedance measurement part configured to measure impedance through the patch; and
- a controller configured to determine whether to apply current to the electrode part based on results of sensing of the wear sensing part and measurement of the impedance measurement part, wherein the wear sensing part comprises a gyro sensor capable of sensing a direction.

9. The electrical stimulation device of claim 8, wherein the impedance measurement part measures bioimpedance or electrode impedance through the patch, and the controller analyze the results of the sensing from the wear sensing part and measurement result from the impedance measurement part and, the controller determines whether the user wears the electrical stimulation device in a correct direction and a measured impedance value is within a preset value range and the controller determines whether that the patch is accurately located at the target position.

10. The electrical stimulation device of claim 8, further comprising:
- one or more of a speaker, a vibrator, a light-emitting device, and a communication part, wherein the controller controls the one or more of the speaker, the vibrator, the light-emitting device, and the communication part based on the results of sensing of the wear sensing part and measurement of the impedance measurement part.

* * * * *